United States Patent [19]

von Halasz

[11] 4,158,023

[45] Jun. 12, 1979

[54] PROCESS FOR THE MANUFACTURE OF OCTAFLUOROPROPANE

[75] Inventor: Sigmar P. von Halasz, Kelkheim, Fed. Rep. of Germany

[73] Assignee: Hoechst Aktiengesellschaft, Frankfurt am Main, Fed. Rep. of Germany

[21] Appl. No.: 888,731

[22] Filed: Mar. 21, 1978

[30] Foreign Application Priority Data

Mar. 23, 1977 [DE] Fed. Rep. of Germany ....... 2712732

[51] Int. Cl.² .................... C07C 17/02; C07C 17/10
[52] U.S. Cl. .................. 260/653.9; 260/653; 260/653.6
[58] Field of Search ................... 260/653.6, 653.9, 653

[56] References Cited

U.S. PATENT DOCUMENTS 3,047,640  7/1962  Sweeney et al. ................ 260/653
3,962,358  6/1976  von Halasz ..................... 260/653.9

FOREIGN PATENT DOCUMENTS 1900241  7/1970  Fed. Rep. of Germany ........ 260/653.6
902590  3/1961  United Kingdom ............... 260/653.6
905617  9/1962  United Kingdom ............... 260/653

*Primary Examiner*—C. Davis
*Attorney, Agent, or Firm*—Curtis, Morris & Safford

[57] ABSTRACT

Octafluoropropane, $C_3F_8$, is prepared by a two-step process. In the first step hexafluoropropene is reacted with hydrogen fluoride in the presence of a chromium oxyfluoride catalyst. The 2H-heptafluoropropane obtained is reacted with fluorine in the presence of a catalyst which contains a subgroup element of the Periodic System as a free metal or as a fluoride. Octafluoropropane is isolated from the resulting gas mixture. Hydrogen fluoride also obtained may be recycled to the first reaction step.

7 Claims, 3 Drawing Figures

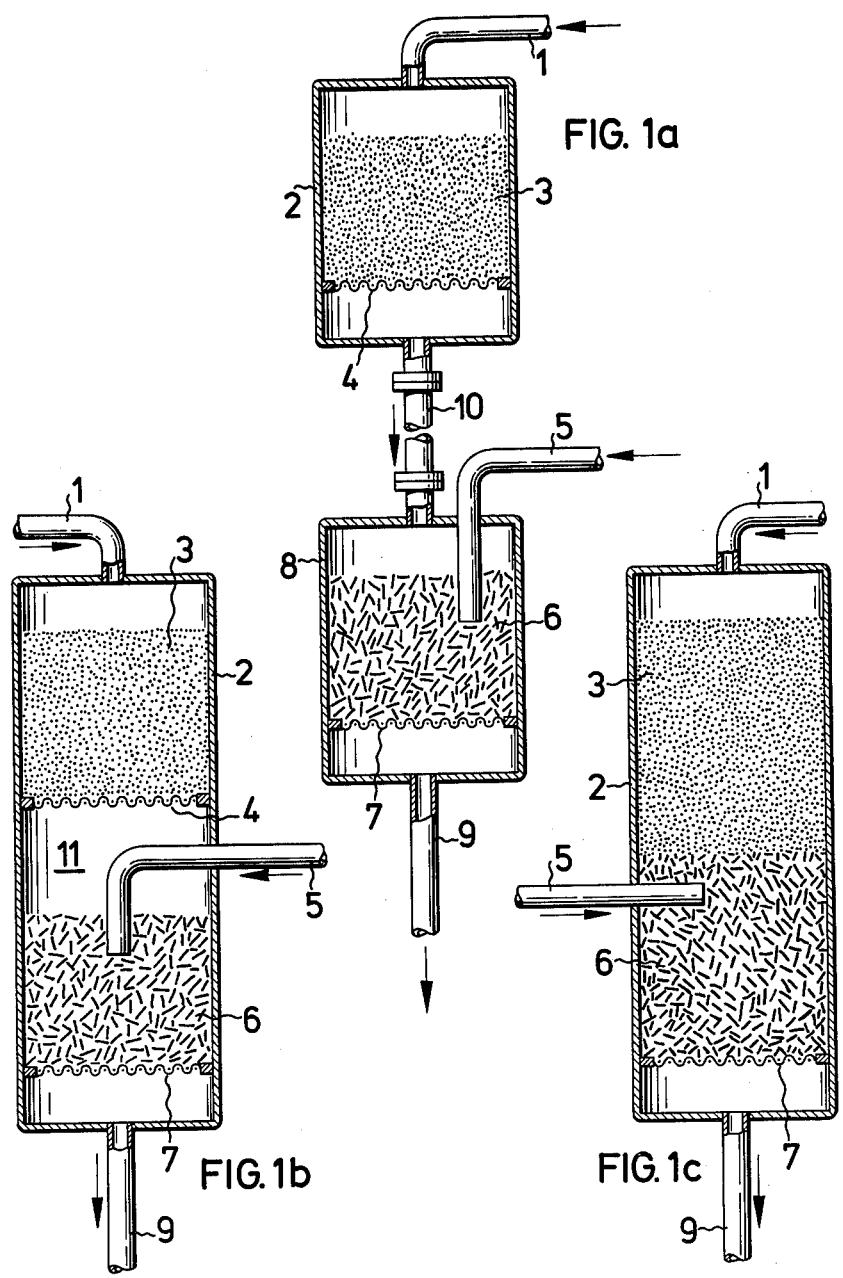

PROCESS FOR THE MANUFACTURE OF OCTAFLUOROPROPANE

The present invention relates to a process for the manufacture of octafluoropropane from hexafluoropropene.

Octafluoropropane, $CF_3CF_2CF_3$, is distinguished by high thermal and chemical stability, incombustibility, high physiological tolerability and excellent properties. Because of its chemical and physical properties, it is used in numerous application fields, for example as an inert reaction medium, as a gas in breathing systems, as dielectric, as component for propellants, as a heat exchanger liquid, as a deep-freezing agent, as fluorine component in H/F lasers, or as an etching agent for $SiO_2$-coated silicium. Therefore, simple and economic processes for the manufacture of this compound are in demand.

The hitherto known processes for the manufacture of octafluoropropane can be classified as follows:

(1) gas phase fluorination of hydrocarbons with or without catalysts, (2) electrofluorination of hydrocarbons in hydrogen fluoride, and electrolysis in salt melts, (3) fluorination of chlorofluoro-alkanes and carbon with fluorine or reactive fluorides, (4) pyrolysis of fluorinated hydrocarbons, (5) fluorination of hexafluoropropene with metal and non-metal fluorides (addition reactions).

Gas phase fluorination of saturated or unsaturated hydrocarbons with elementary fluorine is carried out in the presence of catalysts, for example silver fluoride catalysts (G. H. Cady et al., Ind.Eng.Chem. 39, (1947) 290). When a jet reactor (jet fluorination) is used, gas phase fluorination of hydrocarbons may be carried out without catalysts (E. A. Tyczkowski and L. A. Bigelow, JACS 75, (1953); F. P. Avonda et al., JACS 78, 2798 (1956); A. F. Maxwell et al., JACS 82, 5827 (1960)). Elementary fluorination is possible also with cobalt trifluoride instead of fluorine (E. J. Barber et al., JACS 73, 4214 (1951)). However, in thse processes large amounts of fragments and dimer trimer and polymer products are formed as by-products (tar formation).

A further disadvantage resides in the fact that, per each C-H bond to be substituted, an equivalent amount of hydrogen fluoride is formed inevitably, so that the starting product fluorine is thus converted up to 50% to the HF by-product. The hydrogen fluoride so formed must be either worked up or reused in other fluorination processes, or it is lost in the form of a polluting waste product requiring additional expenditure for its elimination. This disadvantage is inherent in all processes where hydrocarbons are fluorinated.

In the electrofluorination of hydrocarbons, there are obtained the corresponding perfluoro-alkanes with a more or less good yield (J. H. Simons et al., J.Electrochem.Soc 95, 47 (1949)); however, this synthesis method requires considerable expenditure as to apparatus and energy. Moreover, the carbon skeleton is subjected to partial fragmentation (P. Sartori, Angew. Chem. 75, (1963)). Especially the electrofluorination of propane (U.S. Pat. No. 3,840,445) and 1-chloropropane (U.S. Pat. No. 3,709,800) for preparing octafluoropropane requires expensive apparatus and can be carried out in multiple-step operations only if good yields of perfluorinated product are to be obtained. Furthermore, these preparation methods require special measures to be taken for the work-up of the octafluoropropane, in order to remove completely the unreacted $C_3H_8$ propane which causes trouble in many application fields (U.S. Pat. No. 3,887,629).

Reaction of chlorofluoro-alkanes at 350° to 500° C. with fluorine or chlorotrifluoride (U.S. Pat. No. 2,831,035) or manganese trifluoride (U.S. Pat. No. 2,578,721) yield up to 80% of $C_3F_8$ which, however, has to be separated from other chlorine containing fluoroalkanes having a similar boiling point.

Alternatively, preparation of octafluoropropane by thermolytic reaction of fluorinated hydrocarbons has been described. The reaction temperatures required for the pyrolysis of $CHF_3$, that is, 600° to 900° C. (British Pat. No. 971,900), that of $CF_3CHFCF_3$, that is, about 500° C. (British Pat. No. 905,617), and that of $C_3F_6$, that is, 600° C. (U.S. Pat. No. 3,167,592) are too high to be in a still economic range, and moreover, the yields of octafluoropropane obtained are poor.

FLUORINATION OF HEXAFLUOROPROPENE

Several methods have been proposed for the manufacture of octafluoropropane from hexafluoropropene by fluorination with mild fluorination agents, for example nitrosyl fluorides, nitrogen trifluoride, xenon fluorides, sulfur tetrafluoride or antimony pentafluoride. However, these methods are not very important because of the difficult obtention of the fluorination agents and the poor yields of $C_3F_8$.

It is furthermore known to react perfluoro-olefins with elementary fluorine in order to obtain the corresponding perfluorinated alkanes with average yields (W. A. Sheppard and C. M. Sharts, Organic Fluorine Chemistry, 1st. ed., p.53, Benjamin, New York 1969; E. Forche, Methoden der organischen Chemie (Houben-Weyl-Müller), 4th ed., vol. V/3, p. 12, Thieme, Stuttgart 1962; J. M. Tedder, Advances in Fluorine Chemistry (Stacey-Tatlow-Sharpe), 1st. ed., vol. 2, p. 104, Butterworths, London 1961).

Since in the reaction according to the following scheme

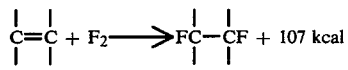

a considerable amount of heat is set free, formation of fragmentation, dimerization or polymerization products occurs very often. Moreover, the reactivity of hexafluoropropene and the oligomers thereof to fluorine increases dramatically according to the following sequence $C_{12}F_{24} < C_9F_{18} < C_6F_{12} < C_3F_6$. While $C_9F_{18}$ can still be reacted with undiluted fluorine at room temperature, $C_6F_{12}$ must be cooled already to $-78°$ C. for this reaction (German Offenlegungsschrift No. 23 32 088).

It has been observed that this process can be applied to the preparation of octafluoropropane from hexafluoropropene and fluorine with special precautions only. The corresponding space-time yields are very poor. When increasing the fluorine amount added, heavy fragmentation occurs (formation of $CF_4$ and $C_2F_6$); when reducing it, dimerization (formation of $C_6F_{14}$) increases.

Therefore, the processes hitherto known can be applied to the manufacture of octafluoropropane with difficulty only.

The object of the present invention is therefore to provide a simple process for the manufacture of octafluoropropane on the basis of hexafluoropropene, which gives good yields and has no polluting effect, and which is not affected by the above disadvantages of the processes hitherto known. The invention as defined in the claims solves this problem.

Both steps of the process of the invention can be carried out in the manner known for catalytic gas reactions. Generally, a gas mixture of hexafluoropropene and hydrogen fluoride is passed through a heatable reactor tube containing a chromium oxyfluoride catalyst. The reaction gas formed may be further reacted directly with fluorine in another reactor containing a metal fluoride catalyst. In the case where an excess of HF was used, unreacted HF may be removed here, for example by washing or condensation. The reactors are made from materials which are sufficiently resistant to hydrogen fluoride and fluorine, such as nickel, steel, copper or platinum, or they are provided with a suitable inner lining, for example of polytetrafluorethylene. Advantageously, both reactions are carried out in one single reactor which is divided into two corresponding reaction zones by means of a suitable arrangement of the catalyst packings. The catalysts may for example be positioned on separate sieves, but they may as well be directly one on top of the other which latter arrangement is of course most simple to effect from the apparatus technology viewpoint. In many cases, it is thus possible to adjust the same temperature in both reaction steps.

It is unimportant whether the gases to be reacted are fed to the catalyst zones from above or from below. Several possible arrangements of the two catalyst zones (gas inlet from above) are shown in FIGS. 1a, 1b and 1c of the accompanying drawing.

In all cases, the $C_3F_6$/HF mixture enters the reactor (2) via duct (1), and passes through the catalyst layer (3) (chromium oxyfluoride) which, in FIGS. 1a and 1b, is arranged on a sieve (4). In FIG. 1c, the catalyst (3) is positioned directly on top of the catalyst (6) (for example silver chips).

In FIG. 1a, the $C_3F_7H$ formed leaves the reactor (2) via duct (10) and flows to the second reactor (8). In FIG. 1b, both catalyst layers (3) and (6) are in the same reactor, separated however by a free space (11).

In all cases, the $C_3F_7H$ formed and flowing downward is mixed in the layer (6) with fluorine fed in via duct (5) which is advantageously dipped into the interior of the catalyst layer (6). The mixture $C_3F_7H/F_2$ is converted to $C_3F_8$+HF in the catlayst (6) lying on the metal sieve (7), and the latter mixture leaves the reactor via duct (9).

The addition of hydrogen fluoride on hexafluoropropene with formation of 2H-heptafluoropropane according to the following scheme

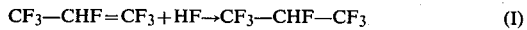

$$CF_3-CHF=CF_2+HF\rightarrow CF_3-CHF-CF_3 \tag{I}$$

is known, and it is carried out in the presence of active charcoal at temperatures of from 250° to 450° C. (British Pat. No. 902,590). However, active charcoal is not sufficiently stable to fluorine. Small amounts of water present result in oxygen containing by-products. Therefore, in accordance with this invention, the presence of water has to be avoided as far as possible in both reaction steps.

The chromium oxyfluoride catalysts used in the first catalyst zone may be prepared for example by treating chromium oxide hydrates with hydrogen fluoride (e.g. according to German Auslegeschrift No. 1,252,182). In their presence, the addition of hexafluoropropene and hydrogen fluoride is nearly quantitative at low temperatures already, and especially proceeds without formation of by-products which adversely affect the following elementary fluorination. In contrast to active charcoal containing catalysts, the chromium oxyfluoride catalyst is stable with respect to elementary fluorine. This means that the subsequent elementary fluorination can be carried out without safety precautions in the same reactor vessel, because a possible penetration of elementary fluorine into the first catalyst zone is not critical.

The chromium oxyfluoride catalysts are non-volatile substances being solid at 100° to 350° C. The atomic ratio Cr:O is generally from 1:1 to 1:2, and that of Cr:F from 1:1 to 1:2.

In the second catalyst zone, a metal fluoride or metal is used as fluorination catalyst. Alternatively, compounds which react with fluorine to form metal fluorides may be used, for example metal bromides. Suitable fluorides are especially fluorides of the 1st, 2nd and 8th subgroup.

As catalytically active metals there may be used the metals of the subgroups of the Periodic System, for example Ce, La, Ti, Zr, Cr or Mn, especially those which do not form liquid or volatile fluorides at the reaction temperature. Apart from the catalytically active metal elements preferably of the 1st, 2nd or 8th subgroup of the Periodic System such as copper, silver, gold, mercury, cobalt or platinum, alloys of these metals may likewise be used, for example copper/nickel alloys (German silver), copper/zinc alloys (brass) or copper/silver alloys (silver solder). Alternatively, coated metals such as platinized steel or gilded copper are suitable as well.

The term "subgroup" covers the groups IIIB (e.g. La) to VIIB (e.g. Mn), VIII (e.g. Pt), IB (e.g. Ag) and IIB (e.g. Zn) of the Periodic System.

Before using for the first time such a metal catalyst in the form of chips, cubes, balls etc., as is usual, it is recommended to subject it to a preliminary fluorination with elementary fluorine at temperatures of from 60° to 250° C., in order to obtain at least a superficial fluorination.

In the reaction of the $C_3F_7H$ with elementary fluorine in dilute or undiluted form, a nearly quantitative substitution of the hydrogen in the 2H-heptafluoropropane occurs according to the following scheme:

$$CF_3CHFCF_3+F_2\rightarrow CF_3CF_2CF_3+HF \tag{II}$$

In the case of optimum utilization of both catalysts, the ratio of their packing volume (1st step: 2nd step) is in a range of from about 1:1 to 1:4, preferably from 1:1.5 to 1:3.

The hexafluoropropene used for the process of the invention is fed in as a gas of industrial-grade purity, advantageously in anhydrous and normally in undiluted form. Dilution for example with $N_2$ or $C_3F_8$ is possible but increases the yield only insignificantly.

The amount of hexafluoropropene to be fed to the first reaction step under atmospheric pressure is from about 1 to 50 liters (about 0.04 to 2.2 mols) per liter of catalyst and hour, but may be smaller of course. Alternatively, at higher pressure and with good cooling, the throughput of $C_3F_6$ may be increased.

Hydrogen fluoride is added advantageously in anhydrous form and generally without dilution. The amount of gaseous hydrogen fluoride fed in is generally from 0.8 to 150 g (or 0.04 to 7.5 mols) per liter of catalyst and hour, and it should be at least equivalent to that of the hexafluoropropene used, but preferably greater. The molar ratio of $C_3F_6$ to HF is for example from 1:3 to 1:1, preferably from 1:2 to 1:1.1, and especially from 1:1.6 to 1:1.2. The total amount of hydrogen fluoride is not critical when an excess (relative to hexafluoropropene used) is employed. Even large excess amounts of HF are allowed; however, separation problems may then arise in the work-up of $C_3F_8$.

An excess of hydrogen fluoride is recommended because thus a quantitative conversion of hexafluoropropene is ensured. Moreover, the presence of excess hydrogen fluoride proves to be advantageous in the subsequent second reaction step: the hydrogen fluoride is thus partially added on hexafluoropropene in the first catalyst zone (chromium oxyfluoride catalyst) (according to reaction scheme I); and it serves as diluent in the second catalyst zone where in any case hydrogen fluoride is formed additionally by the reaction of fluorine with 2H-heptfluoropropane (according to reaction scheme II). The hydrogen fluoride being present in the reaction gas is separated after the elementary fluorination is complete and, if desired, recycled to the first reaction step. Separation of HF from the octafluoropropane can be carried out either by distillation or by condensation in suitable cooling traps. Alternatively, the hydrogen fluoride may be absorbed in sodium fluoride towers and subsequently desorbed under heat. Since hydrogen fluoride is thus preferably circulated in a circuit, it needs to be replenished in small amounts and after prolonged periods of time only, depending on the operation mode, the absorption capacity or the condensation degree in the HF circuit.

According to the process of the invention, the fluorine employed is nearly completely consumed for the synthesis of octafluoropropane, because fragmentation occurs to an insignificant extent only and the hydrogen fluoride required according to reaction scheme I and obtained again according to reaction scheme II is nearly quantitatively reused, in contrast to other elementary fluorination methods (mentioned on p. 2, item 1). The process of the invention proceeds therefore according to the following over-all reaction scheme:

$$CF_3-CF=CF_2+F_2 \rightarrow CF_3CF_2CF_3 \quad (III)$$

Dosage of the fluorine is in principle not critical. Advantagous is a molar ratio of $C_3HF_7$ to $F_2$ of from 1:2 to 1:1, preferably from 1:1.3 to 1:1.05. An excess of fluorine is not critical according to the process of the invention, in contrast to elementary fluorination of hexafluoropropene, because this excess can be removed from the gas mixture remaining after the separation of HF either by washing with a fluorine-absorbent, for example trimers of hexafluoropropene (according to German Offenlegungsschrift No. 23 32 097), or by means of a 20% potassium hydroxide solution. A deficiency of fluorine is not critical either, because, surprisingly, there is no formation of $C_6F_{14}$ in the process of the invention, in contrast to the direct fluorination of $C_3F_6$. In the case of a fluorine deficiency, equivalent amounts of unreacted 2H-heptafluoropropane are obtained in the crude gas mixture, which amounts are easily separated from the octafluoropropane by distillation.

The fluorine may be used per se; generally, however, it is diluted with HF or an inert gas such as nitrogen, argon, helium or a perfluoroalkane. Dilution with HF is preferred. Dosage of the inert gas is not critical; its use is not absolutely required, but advantageous, because dilution of the fluorine current with an inert gas substantially prevents undesirable temperature peaks and fragmentation of the C=C skeleton, thus increasing the yield of $C_3F_8$. The volume ratio of $F_2$ to inert gas or HF is generally from 1:5 to 1:0.1. The proportion of inert gas is advantageously small when using very low boiling inert gases ($<-70°$ C.) in order to avoid large amounts of waste gas. Alternatively, a perfluoroalkane, especially octafluoropropane, may be used as an inert diluent.

The reaction of the first step is carried out at temperatures of from 100° to 350° C., preferably 150° to 300° C., especially 180° to 280° C., and that of the second step at temperatures of from 100° to 350° C., preferably 120° to 280° C., and especially 150° to 250° C. In the case of the preferred operation mode, that is, combination of both reaction steps in one reactor, reaction temperatures of from 100° to 350° C., preferably 150° to 280° C., and especially 180° to 250° C., are advantageously chosen.

The octafluoropropane yield of the process of the invention is around 90 to 95% of the theoretical yield, relative to hexafluoropropene used. The conversion rate of hexafluoropropene is nearly quantitative in the first catalyst zone (chromium oxyfluoride catalyst), that is, from 96 to 99.5% of the theoretical yield. The fluorine used for the preparation of octafluoropropane is consumed to an optimum extent because of the continuous recovery of hydrogen fluoride according to reaction schemes (I), (II) and (III). Fragmentation products ($CF_4$, $C_2F_6$) are formed in insignificant amounts only in the process of the invention (0.5 to a maximum 5% of the theory).

The residence time of hexafluoropropene and 2H-heptafluoropropane in the reactor is not critical, and it may vary in both cases in a range of from 5 seconds to 5 minutes. Since octafluoropropane proves to be stable to fluorine within the temperature range applied, the residence time of octafluoropropane in the reactor is not critical either; an upper limit being set only by technological considerations.

Generally, the process of the invention is carried out under normal pressure; overpressure and underpressure being likewise allowed within wide limits. Thus, operations may proceed at a pressure below 1 bar or above 1 bar up to 10 bars or more, a pressure of from 1 to 3 bars being preferred.

In the case of fluorination on an industrial scale, it is desirable to ensure continuous and uniform manufacturing operations. According to the process of the invention, continuous operations, that is, for example, continuous feed of HF, $C_3F_6$, $F_2$ (optionally diluted with an inert gas), continuous recycling of HF and continuous work-up of octafluoropropane, $C_3F_8$, are especially advantageous, because this results in small amounts of waste water, and a high consumption rate of hydrogen fluoride, hexafluoropropene and fluorine.

It is surprising that the addition of hydrogen fluoride on a perfluoroolefin is possible in the presence of chromium oxyfluoride catalysts, and that this addition can be carried out with nearly quantitative yields even at moderate temperatures. It is furthermore surprising that HF can be used as diluent gas in the second step, resulting in a reduced fragmentation of the C—C skeleton.

The process of the invention brings about a considerable technical progress, because it allows the manufacture of octafluoropropane with yields of more than 90% on the basis of hexafluoropropene easily obtainable on an industrial scale, with optimum consumption of the elementary fluorine used, without wastes of HF, without formation of dimerization products and without substantial amounts of fragmentation products. Because of the high octafluoropropane yields, the simple operation mode at moderate temperatures, and the insignificant proportion of waste water and waste gas, the process is very interesting.

The following examples illustrate the invention.

A. Preparation of 2H-heptafluoropropane from hexafluoropropene

EXAMPLE 1

The reaction of hexafluoropropene, $C_3F_6$, with hydrogen fluoride, HF, is carried out in a vertically positioned copper tube having a length of 150 cm and an inner diameter of 5.3 cm. The reactor tube is provided with a heating jacket on the outside, with thermocouples in the interior, and with a sieve at its lower end. The packing of the tube consists of chromium oxyfluoride grains prepared according to German Auslegeschrift No.1,252,182 by fluorination of chromium oxyhydrate green with hydrogen fluoride. At the upper end of the reactor, there is an inlet orifice with tubular ducts for the feed of gaseous hydrogen fluoride and gaseous hexafluoropropene. To the lower end of the reactor, a further tubular duct is connected for the discharge of unreacted hydrogen fluoride into a receiver filled with water. The deacidified gaseous reaction product is dried in a calcium chloride tower and condensed in glass traps cooled by means of dry-ice.

Starting hydrogen fluoride (HF) of more than 99% purity is taken from a commercial steel cylinder, measured in gaseous form by means of a calibrated differential pressure gage, and fed to the reactor via heated tubular ducts.

Starting hexafluoropropene ($CF_3CF=CF_2$) of 98 to 99% purity is taken from a commercial steel cylinder, dried over phosphorus pentoxide and dosed by means of a calibrated differential pressure gage. An ascension pipe manometer serving simultaneously as safety valve is mounted before the differential pressure gage in order to control the dynamic pressure which establishes itself. The dynamic pressure meters are filled with perfluorinated polyether oil.

At reactor temperatures of 260°–270° C., a total of 245 g (12.25 mols) of HF and 1470 g (9.8 mols) of $C_3F_6$, corresponding to a molar ratio of HF:$C_3F_6$ of 1.25:1, is fed in within 6.5 hours and passed over the chromium oxyfluoride catalyst (800 ml packing volume) contained in the reactor.

2.54 mols of HF are collected in the washing water. Distillation of the washed and dried condensate yields 1605 g (9.44 mols) 2H-heptafluoropropane, $CF_3$—CHF—$CF_3$, having a boiling point of $-16.5°$ to $-17.5°$ C., which corresponds to a yield of 96.3% of the theoretical yield, relative to $C_3F_6$ used. The 2H-heptafluoropropane obtained is identified by means of infrared spectra (Spectra for comparison are available from: D. G. Weiblen, Fluorine Chemistry, vol. II, ed. by J. H. Simons, Academic Press, New York 1954, p. 472, and by $^{19}F$ and $^1H$ NMR spectr (Spectra for comparison are available from: S. Andreades, JACS 86 (1964) 2003), and it is tested for the purity degree by gas chromatography on PORAPAK ® columns (at 100° C.); the purity degree being about 99.1% (remainder: $C_3F_6$ and cyclo-$C_3F_6$).

EXAMPLE 2

In the test apparatus as described in Example 1, a total of 160 g (8.0 mols) of HF and 900 g (6.0 mols) of $C_3F_6$, corresponding to a molar ratio of HF:$C_3F_6$ of 1.33:1, are passed within 4.0 hours at temperatures of 205° to 215° C. over the same chromium oxyfluoride catalyst.

2.18 mols of HF are titrated in the washing water. The subsequent distillation of the condensate yields 975 g (5.74 mols) of 2H-heptafluoropropane, corresponding to a 95.7% theoretical yield, relative to hexafluoropropene used.

EXAMPLE 3

In the test apparatus as described in Example 1, a total of 153 g (7.65 mols) of HF and 1013 g (6.8 mols) of $C_3F_6$, corresponding to a molar ratio of HF:$C_3F_6$ of 1.13:1, are passed within 4.5 hours at 160° to 170° C. over the same chromium oxyfluoride catalyst.

2.06 mols of HF are found in the washing water. The subsequent distillation yields 942 g (5.54 mols) of 2H-heptafluoropropane, corresponding to an 82% theoretical yield, relative to hexafluoropropene used.

B. Preparation of octafluoropropane from 2H-heptafluoropropane

EXAMPLE 4

The reaction of 2H-heptafluoropropane, $CF_3CHFCF_3$, with elementary fluorine, $F_2$, is carried out in the copper tube used in Example 1, the packing of which, however, consisting now of silver-plated copper chips. These silver-plated copper chips (length 20–40 mm, width 4–6 mm, thickness 0.3 to 0.6 mm) were preliminarily fluorinated with elementary fluorine at 100° to 150° C. to form silver fluoride, and the packing volume of the chips is about 2000 ml. Instead of HF/$C_3F_6$, the 2H-heptafluoropropane prepared according to Examples 1 to 3 is fed to the reactor via the opening at the upper end. A gas mixture of $F_2$ and $N_2$ is fed in via an additional tube of stainless steel reaching from above into the zone of the silver-plated copper chips. Another tubular duct is connected to the lower end of the reactor and leads to a trap (for high boiling liquids), and from there to two parallelly connected HF absorption towers packed with sodium fluoride granules. With alternate switching, HF is absorbed from the crude gas mixture at 90° to 120° C. in one of these HF absorption towers, while simultaneously hydrogen fluoride previously absorbed is desorbed at 250° to 290° C. from the other HF absorber. Thus, the hydrogen fluoride formed is nearly completely recovered, collected in a reservoir and reused for addition on hexafluoropropene (see Example 6 et seq.). After having passed the HF absorbers, the crude gas flows through a washing device containing hexafluoropropene trimer, $C_9F_{18}$, in which, at temperatures of 30° to 40° C. unreacted elementary fluorine is absorbed according to German Offenlegungsschrift No. 23 32 097. For complete deacidification, the crude gas mixture is subsequently washed with a 20% aqueous potassium hydroxide solution. After drying in towers containing $CaCl_2$ or $P_2O_5$, the octafluoropropane formed is condensed in traps cooled by dry-ice.

The elementary fluorine ($F_2$) used is taken from a commercial steel cylinder, measured by means of a previously calibrated differential pressure gage and fed to the reactor after dilution with nitrogen. An ascension pipe manometer is mounted before the differential pressure gage similarly to the dosage of hexafluoropropene (see Example 1).

A total of 1634 g (9.61 mols) of $CF_3CHFCF_3$ and 446 g (11.74 mols) of fluorine (diluted with nitrogen in a volume ratio of $F_2:N_2$ of 1:1.2) is passed within 21 hours at temperatures of 200° to 210° C. over the Ag/Cu catalyst prefluorinated with elementary fluorine.

Low temperature distillation of the deacidified and dried condendsate gives as main fraction 1413 g (7.52 mols) of octafluoropropane ($CF_3$–$CF_2$–$CF_3$), corresponding to a yield of 78.3% of the theoretical yield, relative to 2H-heptafluoropropane used. As by-products, there are obtained: about 26 g (0.3 mol) of $CF_4$, 166 g (1.2 mols) of $CF_3CF_3$ and 102 g (0.6 mol) of unreacted 2H-heptafluoropropane; the latter data have been obtained by gas chromatography analyses.

The main product, that is, octafluoropropane, has a boiling point of −36° to −37° C. (−36.7° C. according to J. A. Brown, J.Chem.Eng.Data 8, 106 (1963)), and it is characterized by IR spectroscopy (identical to the indications of D. G. Weiblen, Fluorine Chemistry, vol. II, ed. by J. H. Simons, Academic Press, New York 1954, p. 469) and by $^{19}$F-NMR spectra (identical to G. V. Dyke Tiers, J.Phys.Chem. 66, 945 (1962)).

EXAMPLE 5

A total of 335 g (1.97 mols) of $CF_3CHFCF_3$, 32 g (1.6 mols) of HF and 83 g (2.18 mols) of fluorine diluted with nitrogen (1:1, relative to the volume) are passed with 7.5 hours at temperatures of 210° to 215° C. over the catalyst of the same test arrangement as indicated in Example 4.

In a subsequent distillation of the condensate, 337 g (1.79 mols) of $CF_3CF_2CF_3$, corresponding to a 91% yield relative to 2H-heptafluoropropane used, are obtained. The amounts of by-products are the following: about 0.1 mol of $CF_3CHFCF_3$ (unreacted) and 0.05 mol of $CF_3CF_3$.

C. Preparation of octafluoropropane from hexafluoropropene

EXAMPLE 6

The reactions of hexafluoropropene with hydrogen fluoride (see Examples 1 to 3) and of 2H-heptafluoropropane with fluorine (see Examples 4 and 5) which were carried out separately in the preceding Examples are carried out in this and the following Example in one single reactor. In this case, the hydrogen fluoride which is first added and then formed anew in the fluorination step, as described in Example 4, is absorbed in NaF towers, desorbed semi-continuously and reused again in the process.

For carrying out this combined reaction, 800 ml (packing volume) of a chromium oxyfluoride catalyst as described in Example 1 are charged to the test apparatus and placed on top of the Ag/Cu catalyst as described in Example 4, separated by a sieve.

As in Example 1, HF and $C_3F_6$ are fed in gaseous form to the upper part of the reactor and reacted in the chromium oxyfluoride layer. In the subsequent Ag/Cu catalyst layer, the reaction mixture obtained is reacted with elementary fluorine which, diluted with nitrogen, is fed directly via a stainless steel tube to the Ag/Cu layer.

At temperatures of 200° to 210° C., a total of 61 g (3.05 mols) of HF, 398 g (2.65 mols) of $C_3F_6$ and 114.4 g (3.01 mols) of fluorine diluted with nitrogen in a volume ratio of $F_2:N_2$ of 1:1.5, is fed to the reactor within 5 hours. The molar ratio of $HF:C_3F_6:F_2$ is 1.15:1:1.14.

Work-up is as described in Example 4. Apart from unreacted $C_3F_6$ and $C_3HF_7$, 1.9% of $CF_4$, 3.0% of $C_2F_6$ and 89.3% of $CF_3CF_2CF_3$ are obtained as reaction products.

The contents of the trap are 487 g, the yield of $C_3F_8$ being thus 87.3% of the theoretical yield, relative to hexafluoropropene used. A subsequent low temperature distillation yields 414 g of $CF_3CF_2CF_3$.

EXAMPLE 7

A total of 49 g (2.45 mols) of HF, 297 g (1.98 mols) of $C_3F_6$ and 95 g (2.5 mols) of fluorine diluted with nitrogen in a volume ratio $F_2:N_2$ of 1:1.2 is reacted within 4.5 hours at temperatures of 205° to 220° C. in the test apparatus and arrangement as described in Example 6. The molar ratio of $HF:C_3F_6:F_2$ is 1.23:1:1.26. The condensate has a weight of 366 g.

Apart from unreacted $C_3F_6$ and $C_3HF_7$, the following reaction products are determined by gas chromatography: 0.4% $CF_4$, 2.1% $C_2F_6$ and 91.9% of $CF_3CF_2CF_3$. Thus, the yield of $C_3F_6$ is 90.4% of the theoretical yield, relative to hexafluoropropene used.

EXAMPLE 8

A total of 71 g (3.55 mols) of HF, 386 g (2.57 mols) of $C_3F_6$ and 118 g (3.11 mols) of fluorine diluted with nitrogen in a volume ratio $F_2:N_2$ of 1:1.2, is reacted in the test apparatus as described in Example 6 within 5 hours at temperatures of 210° to 220° C. The molar ratio of $HF:C_3F_6:F_2$ is 1.38:1:1.21. The condensate obtained amounts to 478 g.

Apart from unreacted products (about 1% of $C_3F_6$ and 2.5% of $C_3HF_7$), the following reaction products are determined by gas chromatography: 0.7% of $CF_4$, 2.3% of $C_2F_6$ and 93.1% of $CF_3CF_2CF_3$. The yield of $C_3F_8$ is therefore 92.3% of the theoretical yield, relative to hexafluoropropene used.

EXAMPLE 9

A total of 89 g (4.45 mols) of HF, 416 g (2.77 mols) of $C_3F_6$ and 119 g (3.13 mols) of fluorine diluted with nitrogen in a volume ratio of $F_2:N_2$ of 1:1.4 is reacted within 4.5 hours at 215° to 220° C. in the test apparatus as described in Example 6. The molar ratio of $HF:C_3F_6:F_2$ is 1.6:1:1.13. The contents of the trap amount of 513 g.

Apart from unreacted products (about 1.2% of $C_3F_6$ and 3.6% $C_3HF_7$), there are determined by gas chromatography: 0.9% $CF_4$, 1.7% $C_2F_6$ and 91.8% $CF_3CF_2CF_3$. Therefore, the yield of $C_3F_8$ is 90.4% of the theoretical yield, relative to hexafluoropropene used. A subsequent low temperature distillation gives 465.6 g of $CF_3CF_2CF_3$.

EXAMPLE 10

A total of 42 g (2.1 mols) of HF, 235 g (1.57 mols) of $C_3F_6$ and 78 g (2.05 mols) of fluorine diluted with nitrogen in a volume ratio of $F_2:N_2$ of 1:1.5 is reacted within 4.5 hours at temperatures of 240° to 250° C. in the test apparatus as described in Example 6. The molar ratio of $HF:C_3F_6:F_2$ is 1.33:1:1.31. The contents of the trap amount to 292 g.

Apart from a small amount of unreacted products ($C_3F_6$ and $C_3HF_7$ together about 1%), there are determined as reaction products by gas chromatography 1.2% $CF_4$, 2.2% of $C_2F_6$ and 95.4% of $CF_3CF_2CF_3$. The yield of $C_3F_8$ is therefore 94.4% of the theoretical yield, relative to hexafluoropropene used. In a subsequent low temperature distillation, 274 g $CF_3CF_2CF_3$ are isolated.

EXAMPLE 11 (Comparative Example)

In the test apparatus and arrangement as described in Example 4, without using the HF absorbers, an elementary fluorination of hexafluoropropene is carried out. At reaction temperatures of 200° to 205° C., a total of 415 g (2.77 mols) of $C_3F_6$ and 107 g (2.82 mols) of fluroine diluted with nitrogen in a volume ratio of $F_2:N_2$ of 1:2.5 is passed within 7 hours over the Ag/Cu catalyst.

The condensate of the gaseous products washed and dried consists of about 9 g (0.1 mol) of $CF_4$, about 48 g (0.35 mol) of $CF_3CF_3$, 38 g (0.25 mol) of $C_3F_6$, 15 g (0.1 mol) of cyclo-$C_3F_6$ and 271 g (1.44 mols) of $CF_3CF_2CF_3$, so that its yield is only 52% of the theoretical yield, relative to $C_3F_6$ used.

The liquid collected in the receiver (for high-boiling substances) has a boiling point of 57° to 60° C. and consists of perfluorohexanes (65 g $\triangleq$ 0.22 mol) being a 1:1 mixture of the isomers having the following structures: $(CF_3)_2CFCF_2CF_2CF_3$ (see also S. P. von Halasz, F. Kluge and Th. Martini, Chem.Ber. 106, (1973) 2950) and $(CF_3)_2CF-FC(CF_3)_2$ (see also R. D. Dresdner F. N. Tlumac and J. A. Young, JACS 82 (1960) 5831 and R. D. Chambers, W. K. R. Musgrave and J. Savory, J.Chem.Soc. (1961) 3779).

EXAMPLE 12

A total of 105 g (5.25 mols) of HF, 253 g (1.69 mols) of $C_3F_6$ and 81 g (2.13 mols) of fluorine without dilution with nitrogen is reacted within 5.0 hours at 235° to 245° C. in the test apparatus as described in Example 6. The molar ratio of $HF:C_3F_6:F_2$ is 3.11:1:1.26. The contents of the trap amount to 314 g.

Apart from a small amount of unreacted substances ($C_3F_6$ and $C_3HF_7$ together about 1%), there are determined the following reaction products by gas chromatography: 1.3% of $CF_4$, 1.1% of $C_2F_6$ and 96.3% of $CF_3CF_2CF_3$. Therefore, the yield of $C_3F_8$ is about 95% of the theoretical yield. In a subsequent low temperature distillation, 281 g of $CF_3CF_2CF_3$ are obtained.

What is claimed is:

1. A process for the manufacture of octafluoropropane from hexafluoropropene, which comprises
    converting hexafluoropropene with hydrogen fluoride in a first reaction step to 2H-heptafluoropropane, at a temperature of from 100° to 350° C. and in the presence of a chromium oxyfluoride catalyst, and
    converting in a second reaction step the reaction gas obtained with elementary fluorine to octafluoropropane, at a temperature of from 100° to 350° C. in the presence of a catalyst containing an element of one of the groups IIIB to VIIB, VIII, IB or IIB of the Periodic System or a flouride compound thereof, and subsequently separating the hydrogen fluoride formed from the octafluoropropane.

2. The process as claimed in claim 1, wherein the catalyst of the second reaction step contains an element of one of the groups IB, IIB or VIII of the Periodic System, or a fluoride compound thereof.

3. The process as claimed in claim 1, wherein the fluoride of the subgroup element of the catalyst of the second reaction step is neither liquid nor volatile at the reaction temperature.

4. The process as claimed in claim 1, which comprises recycling the hydrogen fluoride separated in the second step to the first reaction step.

5. The process as claimed in claim 1, which comprises carrying out the reaction in the second reaction step in the presence of a gas inert to fluorine.

6. The process as claimed in claim 5, wherein the gas inert to fluorine is hydrogen fluoride.

7. The process as claimed in claim 1, which comprises carrying out the reactions of the first and second step in the same reactor.

* * * * *